US009330449B2

(12) United States Patent
Newman

(10) Patent No.: US 9,330,449 B2
(45) Date of Patent: May 3, 2016

(54) SYSTEM AND METHOD FOR GROUND BASED INSPECTION OF WIND TURBINE BLADES

(71) Applicant: DIGITAL WIND SYSTEMS, INC., Newtown Square, PA (US)

(72) Inventor: John W. Newman, Newtown Square, PA (US)

(73) Assignee: Digital Wind Systems, Inc., West Conshohocken, PA (US)

( * ) Notice: Subject to any disclaimer, the term of this patent is extended or adjusted under 35 U.S.C. 154(b) by 420 days.

(21) Appl. No.: 13/839,908

(22) Filed: Mar. 15, 2013

(65) Prior Publication Data

US 2014/0267693 A1    Sep. 18, 2014

(51) Int. Cl.
*H04N 5/33* (2006.01)
*G06T 7/00* (2006.01)
*F03D 11/00* (2006.01)
*G01N 25/72* (2006.01)

(52) U.S. Cl.
CPC .......... *G06T 7/0004* (2013.01); *F03D 11/0091* (2013.01); *G01N 25/72* (2013.01); *G06T 2207/10016* (2013.01); *G06T 2207/10048* (2013.01); *G06T 2207/30164* (2013.01); *H04N 5/33* (2013.01); *Y02E 10/722* (2013.01)

(58) Field of Classification Search
CPC ................................ G06T 7/0004; H04N 5/33
USPC .................................................. 348/128, 144
See application file for complete search history.

(56) References Cited

U.S. PATENT DOCUMENTS

| | | | |
|---|---|---|---|
| 3,371,212 A | 2/1968 | Weiss | |
| 3,478,353 A | 11/1969 | Adams, Jr. | |
| 3,810,005 A | 5/1974 | Bennion et al. | |
| 3,922,907 A | 12/1975 | Hurwitz et al. | |
| 4,413,519 A | 11/1983 | Bannister et al. | |
| 4,507,658 A | 3/1985 | Keating | |

(Continued)

FOREIGN PATENT DOCUMENTS

| | | |
|---|---|---|
| EP | 2131037 A2 | 12/2009 |
| EP | 2527649 B1 | 11/2012 |

(Continued)

OTHER PUBLICATIONS

Meinlschmidt, P., et al., "Thermographic Inspection of Rotor Blades", ECNDT 2006—Tu.1.5.3 (2006).*

(Continued)

*Primary Examiner* — Jamie Atala
*Assistant Examiner* — Kathleen Nguyen
(74) *Attorney, Agent, or Firm* — Panitch Schwarze Belisario & Nadel LLP

(57) ABSTRACT

A ground based wind turbine blade inspection system and method consists of a thermal imaging camera configured to detect propagating defects by acquiring thermal imaging data from a wind turbine blade when it is substantially at thermal equilibrium with respect to surrounding air and analyzing the thermal imaging data with a processor to identify thermal effects associated with latent defects caused by internal friction due to cyclic gravitational stresses and wind loads during normal turbine operation. The system permits latent defects to be identified using a ground-based in situ inspection before they become visually apparent, which allows repairs to be made economically while the blade is in place.

15 Claims, 13 Drawing Sheets

(56) References Cited

U.S. PATENT DOCUMENTS

| | | |
|---|---|---|
| 5,146,289 A | 9/1992 | Newman |
| 5,257,088 A | 10/1993 | Tyson, II et al. |
| 5,479,826 A | 1/1996 | Twerdochlib et al. |
| 5,481,356 A | 1/1996 | Pouet et al. |
| 5,543,916 A | 8/1996 | Kachanov |
| 5,748,003 A | 5/1998 | Zoughi et al. |
| 5,818,242 A | 10/1998 | Grzybowski et al. |
| 5,923,425 A | 7/1999 | Dewa et al. |
| 6,153,889 A | 11/2000 | Jones |
| 6,246,483 B1 | 6/2001 | Smith et al. |
| 6,366,734 B1 * | 4/2002 | Beran et al. .................. 396/8 |
| 6,394,646 B1 | 5/2002 | Ringermacher et al. |
| 6,448,924 B1 | 9/2002 | Hafer, Jr. |
| 6,674,531 B2 | 1/2004 | Mahner |
| 6,717,681 B1 | 4/2004 | Bard et al. |
| 6,881,507 B2 | 4/2005 | Milacic |
| 6,891,148 B1 | 5/2005 | Rivera et al. |
| 6,966,754 B2 | 11/2005 | Wobben |
| 6,968,730 B2 | 11/2005 | Schafrik et al. |
| 7,019,537 B2 | 3/2006 | Hazel et al. |
| 7,083,327 B1 | 8/2006 | Shepard |
| 7,083,384 B2 | 8/2006 | Bosselmann et al. |
| 7,095,221 B2 | 8/2006 | Bosselmann et al. |
| 7,283,251 B1 | 10/2007 | Tansey |
| 7,432,505 B2 | 10/2008 | Brummel |
| 7,554,324 B2 | 6/2009 | Gualtieri |
| 7,825,669 B2 | 11/2010 | Parsons et al. |
| 7,889,119 B2 | 2/2011 | Evers et al. |
| 8,120,522 B2 | 2/2012 | Tralshawala et al. |
| 8,174,139 B1 | 5/2012 | Parsche et al. |
| 8,553,233 B2 | 10/2013 | Newman |
| 2001/0050772 A1 | 12/2001 | Meinlschmidt et al. |
| 2004/0236538 A1 | 11/2004 | Wobben |
| 2005/0157313 A1 | 7/2005 | Mendlovic et al. |
| 2006/0181285 A1 | 8/2006 | Friedman et al. |
| 2007/0132461 A1 | 6/2007 | Holmquist et al. |
| 2008/0237466 A1 | 10/2008 | Key |
| 2009/0009641 A1 * | 1/2009 | Asayama ............ H03M 1/1014 348/294 |
| 2009/0201364 A1 * | 8/2009 | Konomura ....................... 348/65 |
| 2009/0201971 A1 | 8/2009 | Goldammer et al. |
| 2010/0103260 A1 * | 4/2010 | Williams ................ F03D 11/00 348/144 |
| 2010/0253569 A1 | 10/2010 | Stiesdal |
| 2010/0303624 A1 * | 12/2010 | Aderhold ................ F03D 11/00 416/61 |
| 2012/0029840 A1 | 2/2012 | George |
| 2012/0141275 A1 | 6/2012 | Hiremath et al. |
| 2012/0253697 A1 | 10/2012 | Frankenstein et al. |
| 2013/0021471 A1 * | 1/2013 | Waterhouse ............... F24J 2/38 348/139 |
| 2014/0118530 A1 * | 5/2014 | Holmes .................. G01N 25/72 348/92 |

FOREIGN PATENT DOCUMENTS

| | | |
|---|---|---|
| GB | 2235604 A | 6/1991 |
| WO | 2007085259 A1 | 8/2007 |
| WO | 2012003372 A2 | 1/2012 |

OTHER PUBLICATIONS

Beattie, A., "Non-Destructive Evaluation of Wind Turbine Blades Using an Infrared Camera", American Institute of Aeronautics and Astronautics, AIAA 99-0046, (1998).*

Zell, H., et al., "Wind Turbine Inspection—New Methods of Remote Non-destructive Inspection of Rotorblades", Dewi Magazin No. 40, pp. 14-22 (Feb. 2012).

Anjar, B., et al., "Feasibility Study of Thermal Condition Monitoring and Condition based Maintenance in Wind Turbines", Elforsk Electricity and Power Production, Elforsk rapport 11:19, pp. 1-26 (May 2011).

Rumsey, M., "NDT, CM and SHM of Wind Turbine Blades at the National Labs", 2009 NREL Wind Turbine Condition Monitoring Workshop, Wind and Water Power Technology Laboratories, Albuquerque, NM, (Oct. 2009).

Hyers, R., et al., "Condition Monitoring and Prognosis of Utility Scale Wind Turbines", Energy Materials, vol. 1, No. 3, pp. 187-203 (Sep. 2006).

International Search Report and Written Opinion dated Jul. 8, 2014 for corresponding PCT/US2014/030328 filed Mar. 17, 2014.

Hung, Y.Y., "Shearography for Non-destructive Evaluation of Composite Structures", Optics and Lasers in Engineering, vol. 24, pp. 161-182, (1996).

Leblanc, B., et al., "Full-Field Inspection of a Wind Turbine Blade Using Three-Dimensional Digital Image Correlation", Industrial and Commercial Applications of Smart Structures Technologies 2011, Proceedings of the SPIE, vol. 7979, pp. 79790L-79790L-12, (Mar. 2011).

Bond, L., et al., "Condition Monitoring Techniques for Composite Wind Turbine Blades", Review of Progress in Quantitative Nondestructive Evaluation, vol. 11B, Proceedings of the 18th Annual Review, Brunswick, ME, Jul. 28-Aug. 2, 1991, pp. 1647-1654 (1992).

Jungert, A., "Damage Detection in Wind Turbine Blades Using Two Different Acoustic Techniques", NDT.net—The e-Journal of Nondestructive Testing (Dec. 2008).

Beattie, A., "Non-Destructive Evaluation of Wind Turbine Blades Using an Infrared Camera", American Institute of Aeronautics and Astronautics, AIAA 99/0046, (1998).

Renshaw, J., et al., The Sources of Heat Generation in Vibrothermography. NDT & E International, vol. 44, Issue 8, pp. 736-739 (Dec. 2011).

Rumsey, M., et al. "Structural Health Monitoring of Wind Turbine Blades".Smart Sensor Phenomena, Technology, Networks, and Systems 2008. Proceedings of the SPIE, vol. 6933, article id. 69330E (2008).

* cited by examiner

SYSTEM AND METHOD FOR GROUND BASED INSPECTION OF WIND TURBINE BLADES

INCORPORATIONS BY REFERENCE

Applicant hereby incorporates by reference, as if set forth fully herein, the entirety of the disclosures of U.S. Nonprovisional patent application Ser. No. 13/731,085, filed Dec. 30, 2012 and having the title METHOD AND APPARATUS FOR THE REMOTE NONDESTRUCTIVE EVALUATION OF AN OBJECT, U.S. Nonprovisional patent application Ser. No. 13/837,145, filed on Mar. 15, 2013 and having the title METHOD AND APPARATUS FOR MONITORING WIND TURBINE BLADES DURING OPERATION and U.S. Nonprovisional patent application Ser. No. 13/840,470, filed on Mar. 15, 2013 and having the title NONDESTRUCTIVE ACOUSTIC DOPPLER TESTING OF WIND TURBINES BLADES FROM THE GROUND DURING OPERATION.

BACKGROUND OF THE INVENTION

1. Field of the Invention

The invention describes method and apparatus for inspecting wind turbine blades on rotating wind turbine generators, from the ground. The invention has utility for remote detection of propagating latent defects, existing damage and broken adhesive bonds within the skin of a wind turbine blade. This permits subsurface defects to be detected before they become too large for repair in situ, which provide significant economic advantages, as the cost of repairing the wind turbine blade in situ is typically 10% of the cost of replacing a blade.

2. Description of the Related Technology

Due to their large size, extensive surface area and complex shape, wind turbine blades are difficult to non-destructively inspect even within a fabrication or repair facility. Visual inspection cannot identify defects below the surface of the outer skin of the wind turbine blade, which typically is fabricated from a fiberglass material. Active thermography inspection techniques are effective for near surface defects but can give false positives and false negatives due to variations in material thickness and surface emissivity. Angle beam ultrasonic techniques are very slow and may not work through thick carbon fiber spar caps. As a result, blades are commonly installed on towers and put into service with a significant probability of latent manufacturing defects. Furthermore, composite blades are subject to extreme temperature variations. Entrapped water in blades can undergo freeze/thaw cycles, which can cause internal damage. Cyclic forces of gravity and varying forces from the wind acting on the blades as they rotate can cause fatigue damage or the propagation of latent defects over time while manufacturing process mistakes can lead to early blade failure. Defects can grow below the surface of a wind turbine blade to the point that by the time cracks and damage breach the surface and can be detected visually, the damage may not be repairable on tower.

Detecting progressive subsurface damage and propagating defects in wind turbine blades in situ is difficult for a number of different reasons. Inspectors using sky cranes or rope access are expensive, time consuming and put personnel in a very dangerous working environment. While on tower, close access allows inspectors to visually detect blade defects such as trailing edge splits, cracks, lightning damage and blade erosion. In addition, major subsurface delaminations, cracks, debonded of adhesive joints can easily go undetected with current technology.

Access to a wind turbine blade in situ with portable instruments for nondestructive testing also requires rope access or sky platforms and cranes. Blade and tower crawlers with nondestructive testing sensors for in situ inspection have been developed and tested, but they can be prohibitively expensive, slow to operate, require repair and maintenance themselves. Their effectiveness is also questionable. Microwave and radar scanners, while effective for dielectric materials do not work on critical components such as spar caps manufactured that have electrically conductive carbon fiber materials.

There accordingly exists a need for a fast, cost effective nondestructive inspection system and method for wind turbine blades to detect latent and propagating damage early enough to allow on-tower repair before it becomes necessary to remove the wind turbine blade from the tower and repair it off-site or replace it with a new blade.

SUMMARY OF THE INVENTION

Accordingly, it is an object of the invention to provide a fast, cost effective nondestructive inspection system and method for wind turbine blades to detect latent and propagating damage early enough to allow on-tower repair before it becomes necessary to remove the wind turbine blade from the tower and repair it off-site or replace it with a new blade.

In accordance with the embodiment described herein, a system for inspecting utility scale wind turbine generator blades from the ground for propagating subsurface anomalies during normal operation, comprised of a camera sensitive to the thermal emissions from defects subjected to cyclic strain from gravity and wind loading and a means to process thermal images of these emissions to determine location, signal to noise ratio, size or other quantitative measurements and that such early detection may allow repair of the blade up tower instead of more costly replacement.

A second embodiment includes a means to stabilized the thermal images of a wind turbine blade over at least several successive video frames to reduces the image degrading effects of blade motion.

A third embodiment includes a means of stabilizing the camera when making inspections of off shore wind turbines from a boat.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
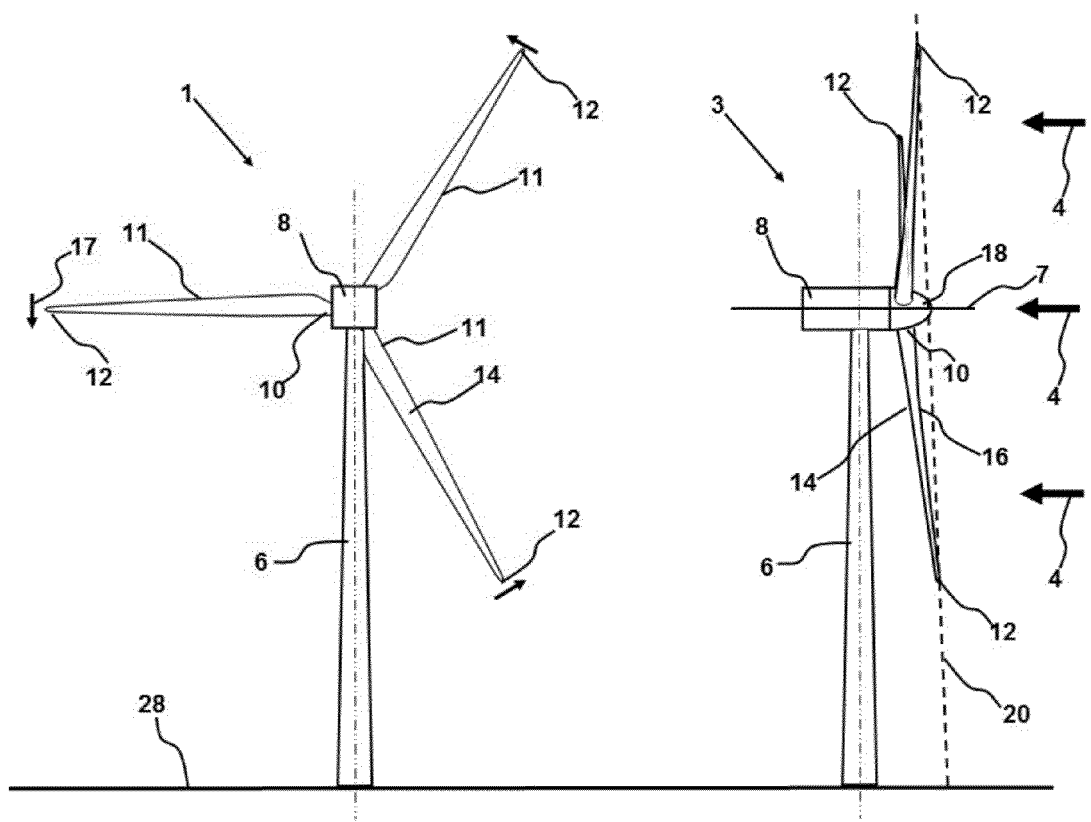
FIG. 1 is a schematic representation of a utility scale, horizontal axis, wind turbine generator.

The embodiments of the present invention disclosed herein, describes a system and method for the nondestructive inspection of wind turbine blades suitable for both onshore and off-shore wind power generators and capable of detecting propagating defects or damage during normal turbine operation. Inspections are made from ground or sea level without any requirements for access to the wind generator tower or any disruption of power generation. Large utility scale wind power turbines are generally of the HAWT design using composite air foil shaped blades to generate the rotational torque needed to drive the electrical generator. Current utility scale wind turbine blades may range from 9 m in length up to more than 50 m, with much larger blades being designed for off-shore wind power generators. The application of this invention may achieve good results on blades of all lengths manufactured with thermoelastic composite materials such as fiber glass and carbon fibers in an epoxy matrix.

Wind turbines blades, during normal operation, are subjected to continuous cyclic loading due to gravity and variable wind forces. Thermal imaging of blade anomalies requires the test be conducted after sunset or on cloudy days during normal operation. After the blades have come to thermal equilibrium with the ambient air temperature the only remaining thermal emissions from the blade occur at the site of propagating damage anywhere in the blade. Tribological damage including plastic deformation, fretting, adhesive wear, oxidation, and phase transformations, such as melting can occur at rubbing crack faces. C. J. Pye et al. (Ref 1) where cyclic gravitational loads pass through structural anomalies. Heat is generated by three mechanisms (J. Renshaw, Ref 2) internal frictional rubbing of contacting surfaces (asperities) on crack walls, deformation of the plastic zone surround the crack, and viscoelastic losses.

While the local blade surface temperature anomaly is small and the area may be small, the present invention provides excellent signal to noise ration and quantitative data to evaluate the condition of the blades. Telephoto optics are necessary to resolve the small angle $\alpha$ subtended by for example a 6 inch long crack at 300 ft. height, where $\alpha$=arc sin $1/600$=$0.0955°$ or only 343 arc seconds. Further, if the defect is located near the blade tip, the thermal indication will be moving at a high rate of speed. For example, on a typical 50M blade operating at 20 rpm, the thermal indication will be moving at 176.8 ft./second.

Depending on the characteristics of the thermal camera, which commonly uses a relatively slow micro bolometer thermal sensor, the rotation of the blade through the field of view typical thermal camera makes it difficult for an operator to see much less analyze the thermal indications, even if the camera has the thermal resolution performance to detect the emissions at all. Positioning the thermal camera on the right side of the tower (on the ground or at sea level for an off shore turbine with ones back to the wind) at a location approximately mid-span under the turbine rotor disk (the plane containing the blade tips) allows the camera to image the leading edges of the turbine blades as they move directly towards the camera with the angle of the blade changing relatively slowly. Good results for defects on the blade leading edges can be obtained. The trailing edges may be inspected in the same manner from the left side of the tower (with ones back to the wind) where the blades are moving directly away from the camera. Imaging a defect that is located elsewhere on the blades is more challenging since the blades are viewed up or down wind of the turbine disk and the image moves rapidly across the field of view of the camera.

The thermal images of the rotating blades from positions upwind or downwind of the plane of the turbine disk can be captured with the thermal camera using the camera memory, if present, or a computer with the appropriate drivers for capturing digital images using a GigE or camera link interface or an analog to digital video frame grabber or any other appropriate camera/computer interface well know in the art. A software algorithm to display each frame by frame in a series of sequenced images allows defects to be identified as the blade rotates into view of the camera. Part of this invention also includes a peak-store image function that records the stored maximum value for each pixel in each frame. As a hot spot on the blade, caused by stress induced internal friction at the site of a propagating defect, plasticity or thermoelastic emissions, rotates into view, each pixel is locked to its maximum value. With a series of sequential frames combined into one peak stored image the motion trajectories of defect indications are recorded through each blade pass. Because wind turbine blades are painted to reflect heat from the sun, the heat from sources other than active defects in the blade may appear in the thermal images of blades as reflections. On example might be the heat from a car situated near the wind tower. Heat signal from a defect will form a sine wave trajectory track around the blade path, while reflection of heat sources on the ground or on adjacent towers appear "painted" on the image of the blade through a small number of frames or a small angle of blade rotation.

In multiple embodiments of this invention a blade image de-rotation stabilization device can be added to the front aperture of the thermal camera to derotate the motion of the blade as it passes through the camera field of view.

A two axis mirror motion using two actuators would allow more precise image motion compensation as the blade is viewed from a distance of from 100 feet to 1000 feet with frequently a considerable off-axis view. As such, the blade motion and the motion of any thermal emitters on the blade surface appears to move in a combined vertical and horizontal motion approximating a sine wave. Blades are best inspected when within approximately 45 degrees of the 90 and 270 degree horizontal position so that the images across the span of the blade have approximately the same scale.

The output signal from a function generator producing a ramp function can be used to drive a voice-coil linear actuator at an amplitude and repetition rate required stop the appearance of motion for several video frames. As the blade starts to pass through the field of view, the mirror pivot motion starts and tracks the blade image across the field of view. The frequency and amplitude can be set with each cycle corresponding to the turbine rotational period τ seconds to track one blade or τ/3 to track all three blades sequentially. Other embodiments include the use of the graphical target generated by software that is place on the video image from the thermal camera that triggers the de-rotator to initiate a mirror motion cycle. As the blade enters the thermal camera field of view and crosses the graphical target on the display, the computer starts to move the mirror to approximately track the blade as long as possible allowing the thermal camera time to capture multiple high quality images. The de-rotator motion may also be triggered by a photo detector established to detect light from a laser beam illuminating the blade from the ground. The unexpanded low power laser and detection electronics would provide an electronic trigger signal when the blade was in the correct position to start tracking.

In another embodiment, a light weight thermal camera can be mounted to a hinged plate and operated with any of the methods for image de-rotation of the rotation blade as describe herein.

Referring now to the drawings, wherein like reference numerals designate corresponding structure throughout the views, and referring in particular to FIG. 1, is a schematic diagram of a HAWT that is typical of both land based and off-shore turbine generators. The view 1 from behind the turbine facing the wind includes tower 6 extending up from the ground or ocean surface 28 to support the nacelle 8 which contains the generator and gear reducers, unless it is a direct drive generator. There are typically three blades, 11, on a utility scale wind turbine having root ends 10 and blade tips 12. As seen from the side view 3, the blade root ends attach to the rotatable hub 18. Blade side 16 facing the wind 4 is often referred to as the high pressure side. The blade side 14, facing away from the wind is referred to as the low pressure or suction side. As the blade speed 17 increases, the blade pitch is adjusted to the optimal angle of attack to the wind 4 to create the maximum lift and torque required to drive the electricity generator.

Figure 2:
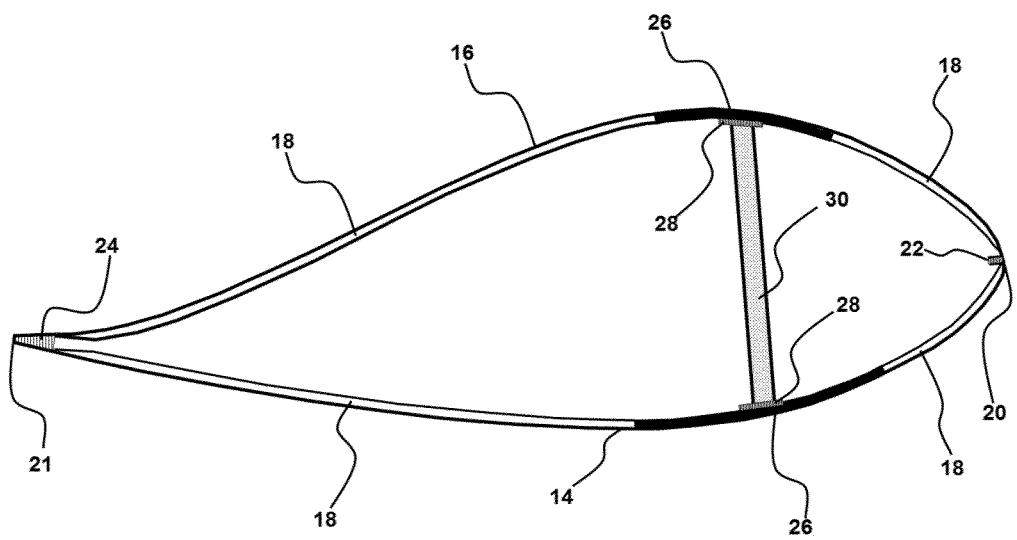
FIG. 2 is a schematic representation of a wind turbine blade cross section.

FIG. 2 shows the construction cross section of a typical HAWT blade. Wind turbine blades are generally manufactured with adhesively bonded composite shells forming the high pressure side 16 and the low pressure side 14. The trailing edge 21 is formed by the adhesively bonded shells 14 and 16 as is the leading edge 20, with adhesive bonding in some cases between two flanges 22 formed by the inner and outer fiberglass skins that make up sandwich panels 18. Two spar caps 26, which may be made from fiberglass or carbon fiber laminate or other composite material, are bonded to the edges of the sandwich panels 18. The blade spar web 30, which can be a solid fiberglass laminate or a sandwich construction with fiberglass or carbon fiber face sheets and a core material made with foam, balsa wood or other suitable material with high compressive strength. The spar web 30 is bonded with adhesive 28 to the spar caps 26 to form an I beam. Sometimes a second or even third spare web is present forming a box beam. Defects such as adhesive disbonds or unbonds present at the spar cap 26 to spar web 30 adhesive bond 28 may lead to catastrophic failure of the blade in service. Fiber waves in the solid spar cap 26 laminate can also lead to cracking and ultimately to blade failure. Further, trailing edge 21 splits or cracks in the high pressure 16 and low 14 pressure side shell adhesive bond 24 may be signs or excessive blade flex during operation. The trailing edge 21 adhesive bond 24, in the area of greatest blade chord width towards the root end 10 supports blade twist loads. Cracks and breaks in the adhesive bond 24 at these locations can also lead to blade failure unless detected in time and the turbine shut down and promptly repaired.

Figure 3:
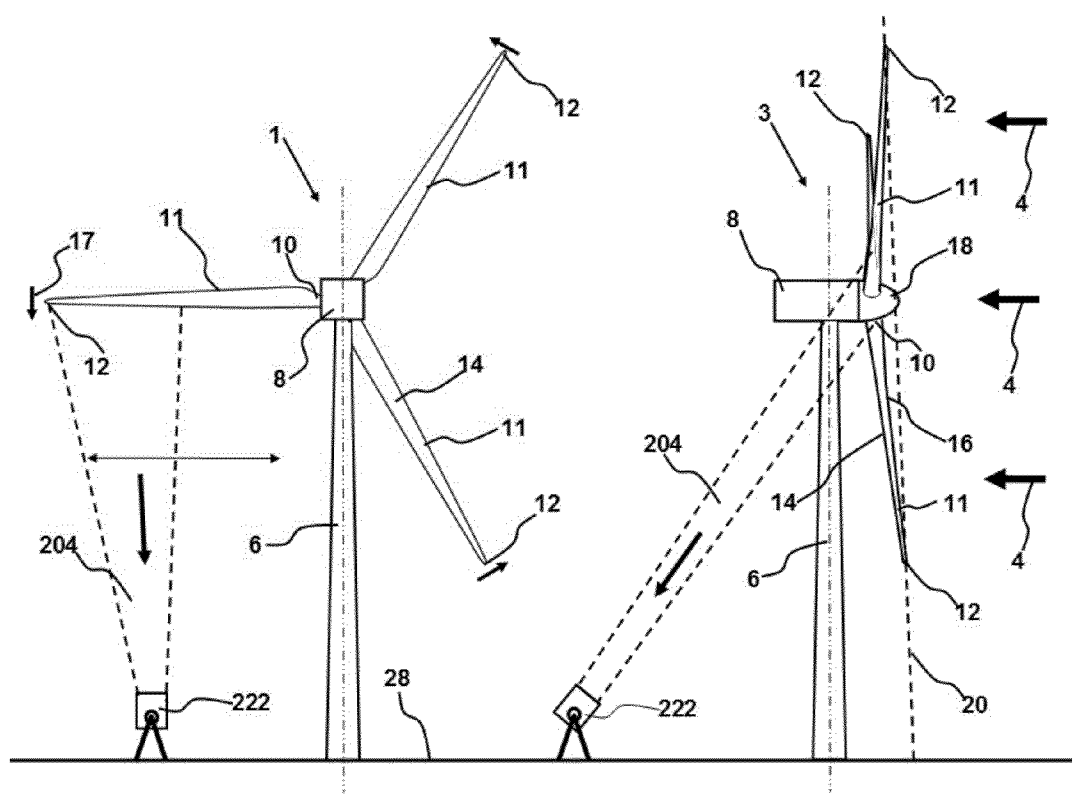
FIG. 3 is a schematic showing the relative location of the thermal camera for inspection the wind turbine blades then orient approximately parallel with the ground or sea level.

FIG. 3 is a schematic diagram showing the side view of thermal camera 222 at locations down wind of tower 6 for inspection of the low pressure side of the blade 11. Thermal emissions 204 from defects in the blade 11 propagating due to cyclic stress load do to gravity and wind fluctuations are detected by thermal camera 222. The side view also shows the plane 20 as a line extending to the ground or sea level 28, containing the blade tips 12. This approximate location is a good viewing position for blade 11 leading edge 20, inspections.

Figure 4:
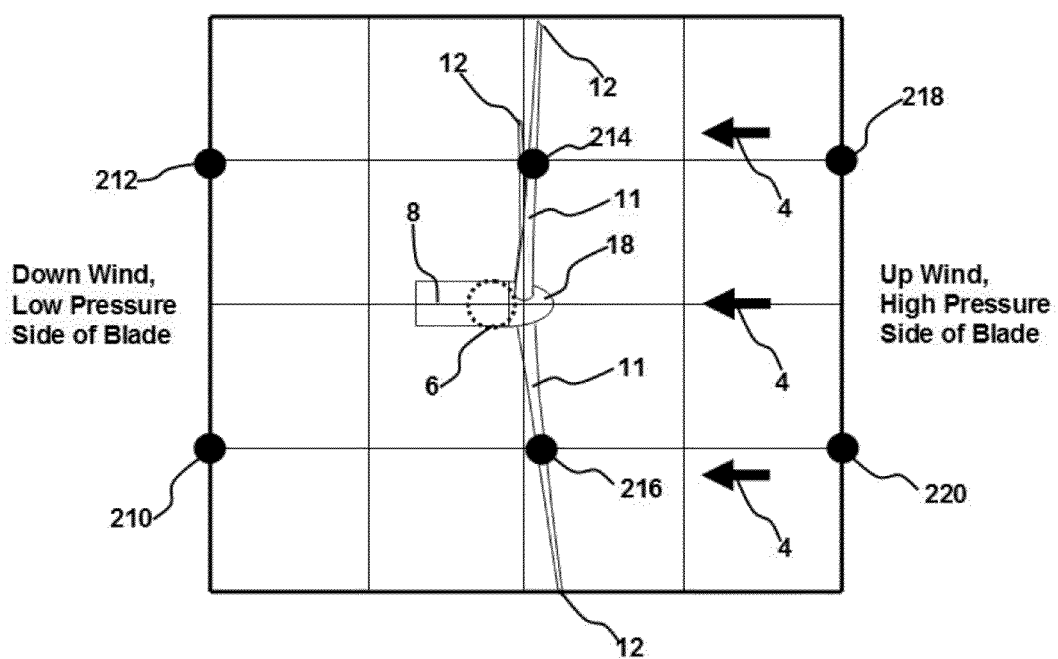
FIG. 4 shows a plan view of a wind turbine site with six locations for the thermal camera to view various locations on the blades.

FIG. 4 shows thermal camera 222, positioned at locations both on the up wind-high pressure side of the turbine blades, at two locations on either side of the tower in the plane of the blade disk and at a location on the down wind, low pressure or suction side of the blades to provide advantageous viewing of the entire blade surfaces during rotation. For the best view angle of the low pressure side 14 of the blades 11 is achieved with the thermal camera 222 positioned at approximately location 212, however the best results are obtained using an image stabilizer as described here in or an image peak storage unit or software due to the relatively high speed the image of the blade passes through the camera field of view. The best view of the blade leading edges 20 are at position 214, in the plane 20 of the blade tips, since the blade 11 is rotating down directly at the camera and the angles of points on the leading edge 20 are changing relatively slowly. Moving down wind from position 214 gives good views of the forward low pressure side surfaces 14, of the blade 11 with relatively low rate of angle changes over three to four video frames. Position 216 is excellent for the trailing edge 21 of the blades and position 220 offers a full view of the high pressure side 16 of the blade 11, which is best viewed with the image stabilizer or peak storage embodiment described herein. Position 210 offers relatively poor views the low pressure side except for the trailing edge 21 and the aft low pressure sandwich structure 18, but with fast moving angle changes and with the blade twist. Wind turbine farms are often located on hills or mountain ridges with little room to move away from the tower 6. Local conditions and land shapes often dictate where the best viewing angles can be obtained.

Figure 5:
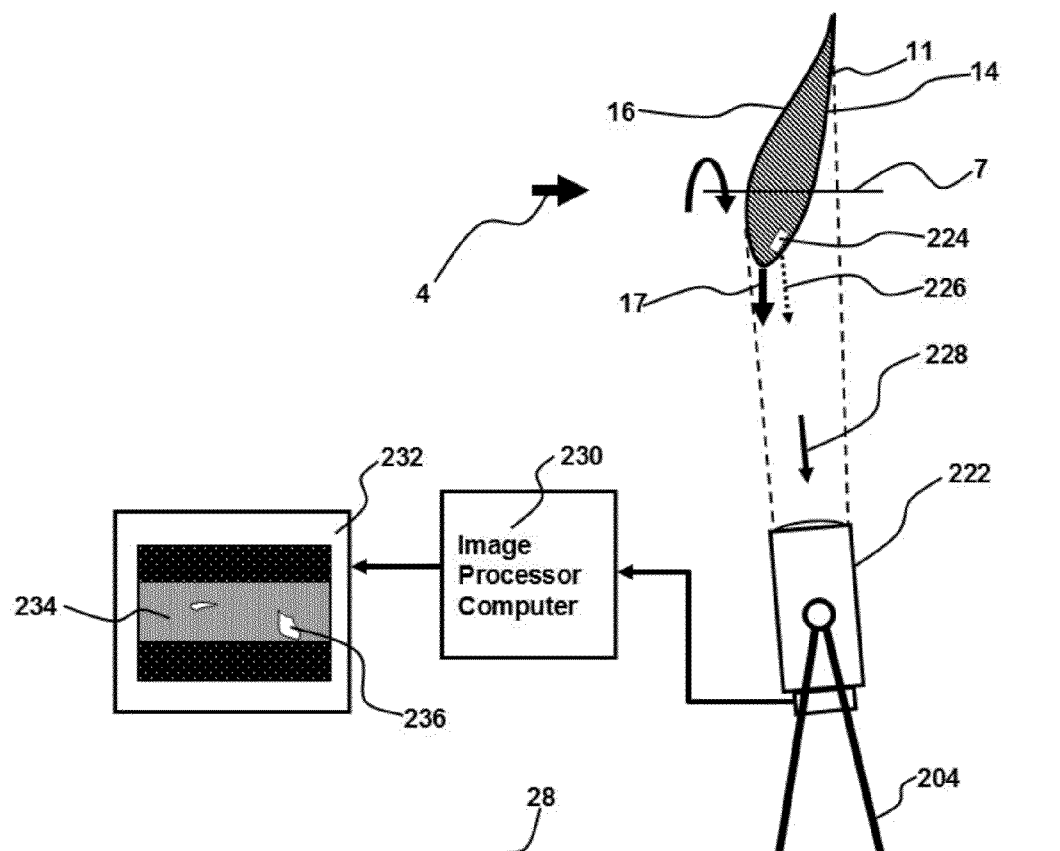
FIG. 5 shows a basic thermal imaging set up suitable for direct viewing and recording blade surfaces in or near the turbine blade disk.

FIG. 5 is a schematic diagram showing a thermal camera 222, positioned to receive low level thermal radiation 228 from the blade 11 due to thermoelastic emission from the stresses acting on the blade material due to gravitational forces from the blade rotation motion 17.

Emission 226 from the mechanically stressed defect 224 appears warmer in the image produced by thermal camera 222 due to internal friction and plasticity around defect 224.

The camera 222 is positioned under the blade at position 214 to receive thermal radiation 228 from the leading edge and the forward part of the low pressure side 14. This position reduces the angular changes due to blade rotation in the image during the frame acquisition. The streamed video images from the thermal camera 222 are recorded by Image Processing computer 230, or in a memory device in the thermal camera 222 as video files, and processed presented using peak store or other image processing techniques and presented on monitor 232. Various means of processing the images including video image peak store, frame by frame analysis, histogram normalization, unsharp filters and so on to obtain good image quality and quantitative measurements of size and location comparing features of known size at the range to the target.

Figure 6:
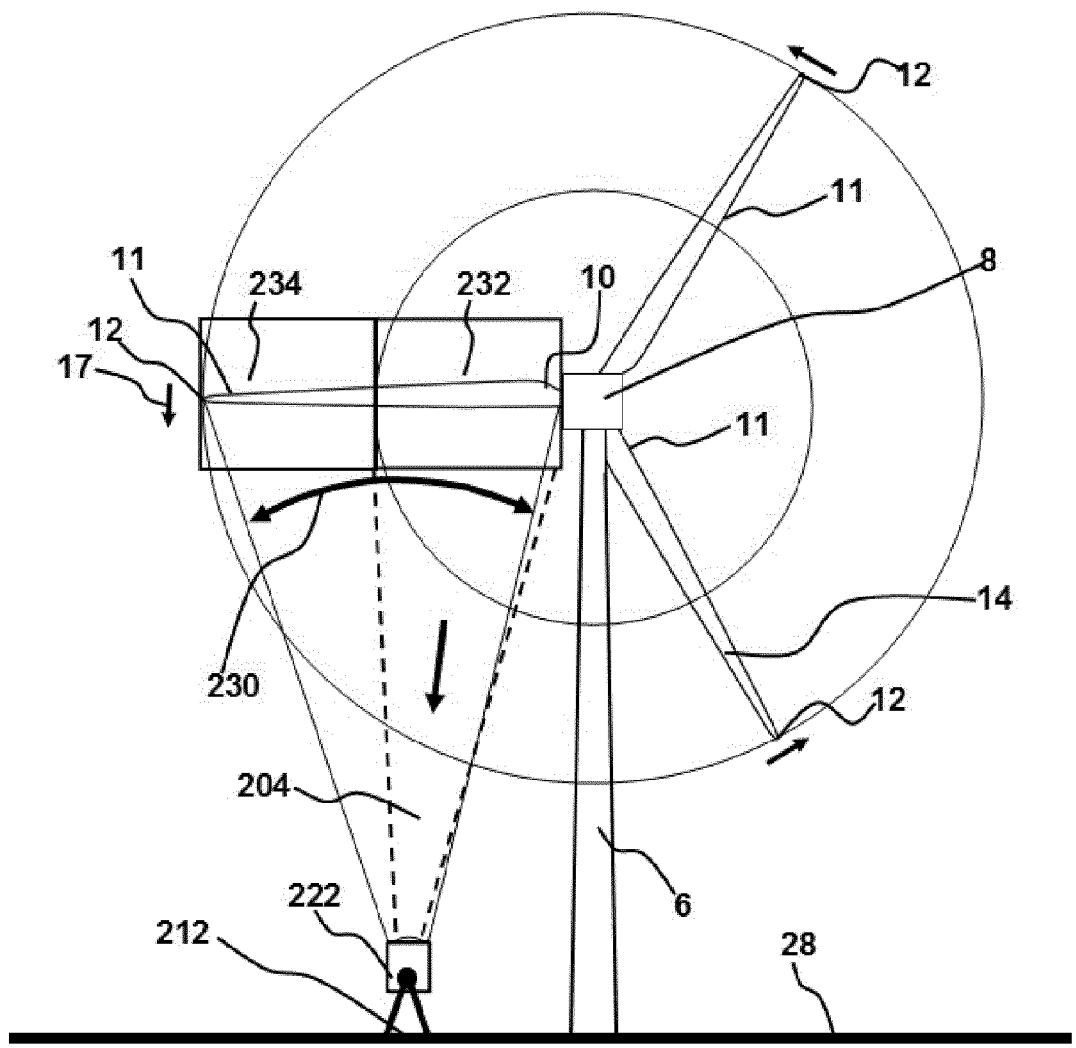
FIG. 6 a schematic showing the thermal camera viewing a low pressure, or suction side of a blade in the horizontal position.

FIG. 6 shows how a thermal camera located at position 212 can be used to test the entire blade from one location by pointing to a blade section inboard adjacent to the generator nacelle 8 and acquiring the thermal image sequences. The moving the camera in an arc 230 outboard and overlapping the next blade section and so on until the tip is reached. The use of programmed servo or other motor drives to move the camera would allow for a fast automated test.

Figure 7:
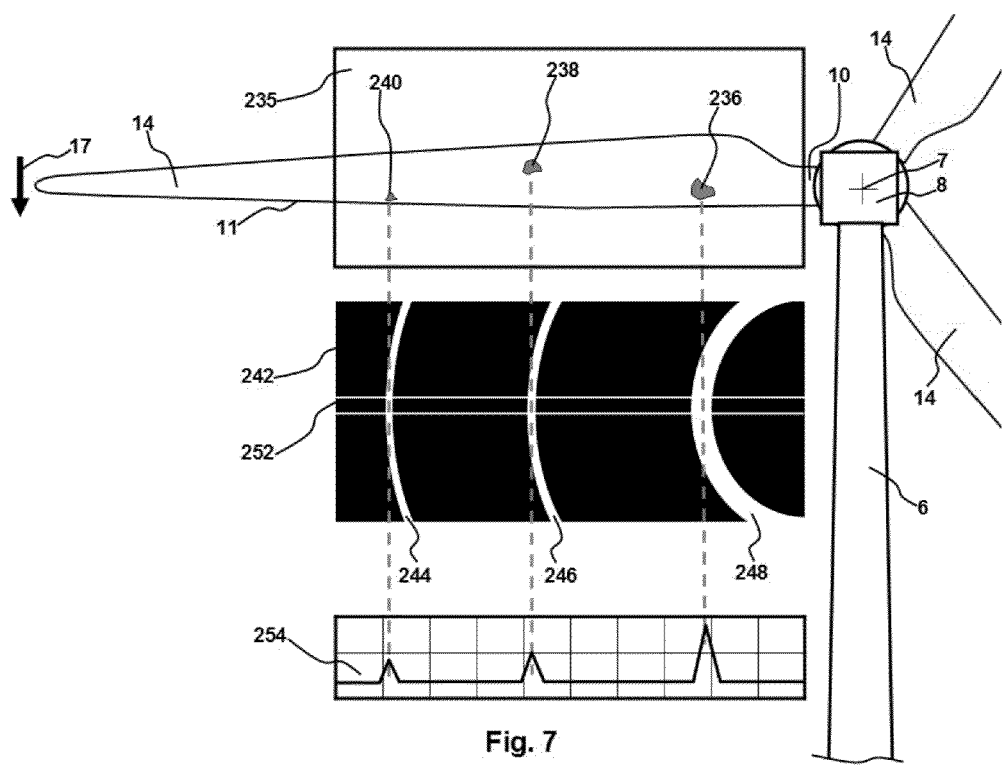
FIG. 7 shows how an electronic image peak store unit captures the trajectory of thermal emitting defects as the blade passes through the thermal camera field of view.
Figure 13:
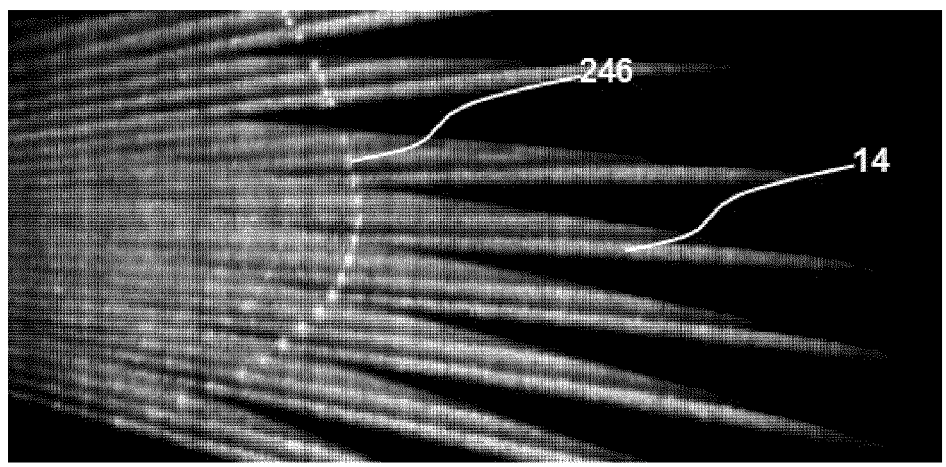
FIG. 13 is a photographic depiction of image frames showing testing performed according to an embodiment of the invention.
Figure 13:
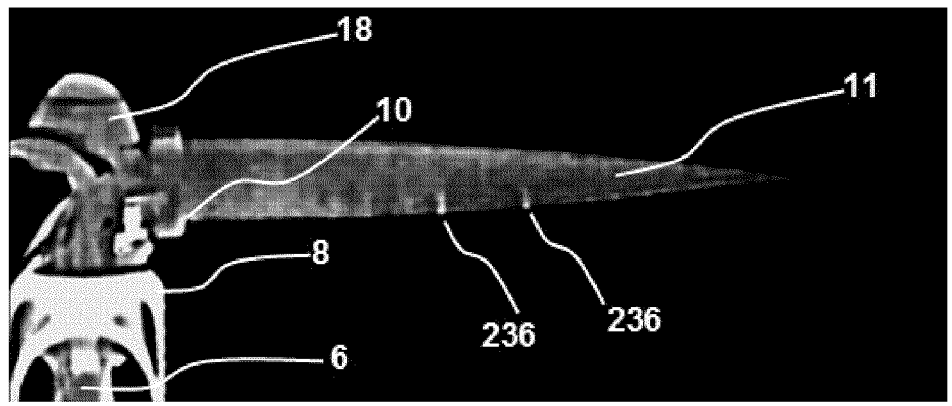

FIG. 7 shows a representation of the video peak store function. The thermal emitting defects 236, 238 and 240 on blade 11 as shown, rotate counter-clockwise in this view of the low pressure side 14 of blade 11, as seen from down wind of tower 6. The axis of rotation 7 is shown in the approximate middle of the nacelle 8. The larger thermal emitting defect, 236, happens to be the closest defect to the axis 7 and generates the strongest signal 248. In a peak stored image, each pixel is locked to the highest gray level value while image data is being acquired by the post-test analysis software or in the field during the test. The result is sources of thermal emissions can be tracked through the field of view as show in defect traces 248, 246 and 244. and as shown in FIG. 13. A thermal emitting defect has a trajectory following the blade in rotation as viewed greatly off-axis. A line scan, 252 through the peak stored image 242, maps the gray level value for each pixel in a line from one side of the image to the other and allows a graph 254 to be plotted showing the gray level signal intensity vs. position on the blade. The distance scale is calibrated in software from the size of know features on the nacelle 8 or tower 6. These values can be corrected mathematically for the difference in velocity for different span wise locations on the blade using a look up table (LUT) or other techniques for correcting image data based on geometric parameters well know in scientific programming and photogrametry.

Figure 8:
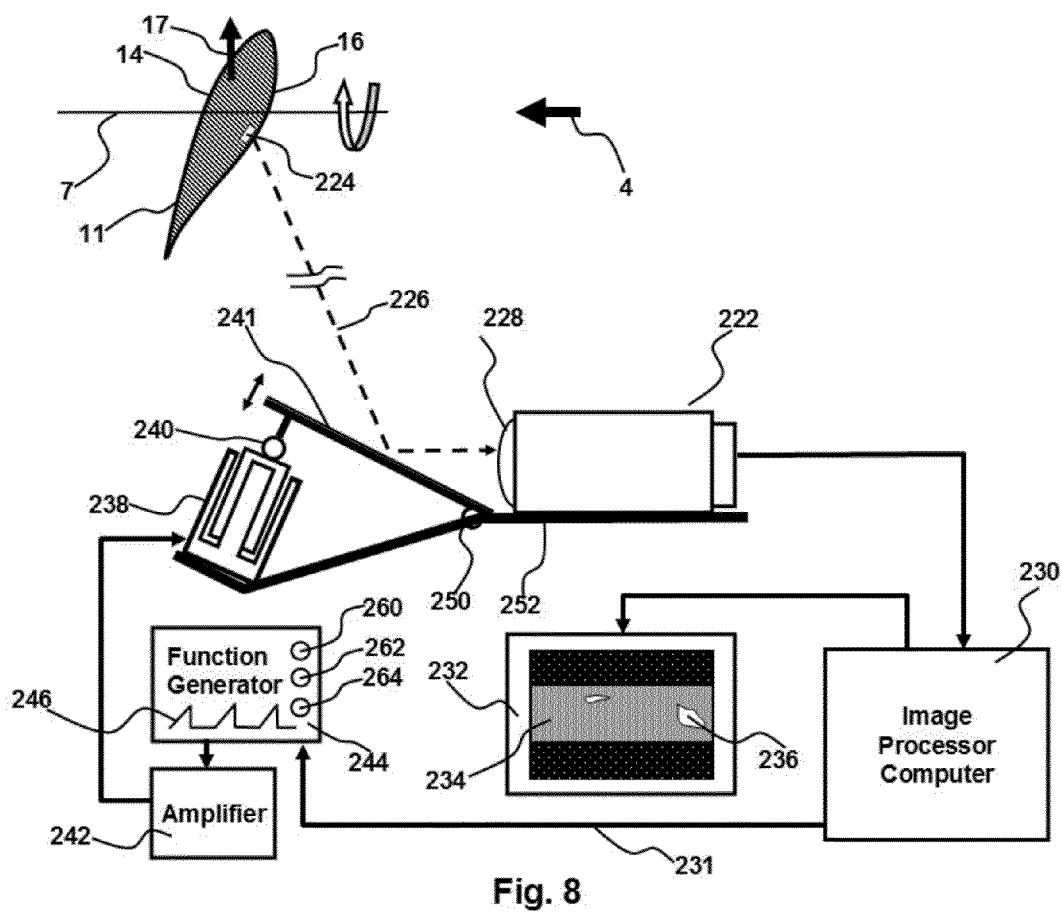
FIG. 8 is a schematic diagram of a manually controlled moving mirror assembly mounted in front of the thermal camera to stabilize, or derotate, thermal images of a rotating turbine blade and suitable for use when the blade is in approximately a horizontal orientation.

FIG. 8 shows one embodiment of the thermal image derotator consisting of a mirror 241, attached to a hinge 250 at one end and the opposite end is connected to a linear actuator or voice coil linear actuator 238 through a ball joint or universal joint 240, whose cyclic motion in the direction of the blade motion can be adjusted to track the approximate motion of each blade 11 as it rotates through the field of view. The derotation will essentially stop the rotation motion for several frames. The blade appears to hang in space giving the thermal camera time to generate higher resolution images of the moving blade. The adjustments consist of amplitude of the ramp voltage 260, which will compensate for the speed of blade rotation, the duration of the ramp function 262, and the time 264, between each start of the ramp function. The output of function generator 244 is amplified in amplifier 242 which then drives the linear motor actuator 238. The motion of mirror 241 can de-rotate short sequences of images produced by thermal camera 222. By selecting the repetition rate, 262, the user can select to image all the blades by starting the tracking motion every τ/3 seconds, where τ=the period of rotation of the turbine in seconds or by selecting a repetition rate of τ, the images of the same blade 14, will be presented and de-rotated. A spring can be used to provide a restoring force to bring the mirror back to its start position, ready for the next blade pass. Only one or more video frames need to be tracked to substantially improve blurring of the thermal camera image due to blade rotation. The frequency of motion of the de-rotating mirror 241, can be calculated in the following example. Assume a turbine operating @ 15 rpm, a thermal camera 222 with a 30 frames per second frame rate, and it is desired to de-rotate 4 video frames. The period, {fourth root}, of the turbine is the time required to make 1 revolution, in this case 60 seconds/15 rpm=4 seconds. In this time, the thermal camera 222 (operating at 30 frames/second) captures (4 seconds×30 frames/second)=120 frames. The 4 frames we wish to de-rotate are captured over a time of (4 frames/30 frames/sec.)=0.133 seconds. To de-rotate these four frames then, we start moving the mirror to track the blade starting at 0 seconds, when the blade 14 enters the field of view of the thermal camera. The mirror 241, angle is changed (increased or decreased depending on what direction the blade is moving through the field of view) continuously over 0.133 seconds, then returned to the start position. To track only one blade, the tracking motion is started every 4 seconds (τ). To track all three blades sequentially, the tracking motion is started every τ/3 seconds, 4/3=1.33 seconds. After each tracking motion, the mirror is returned to the start position to await the next tracking cycle.

Figure 9:
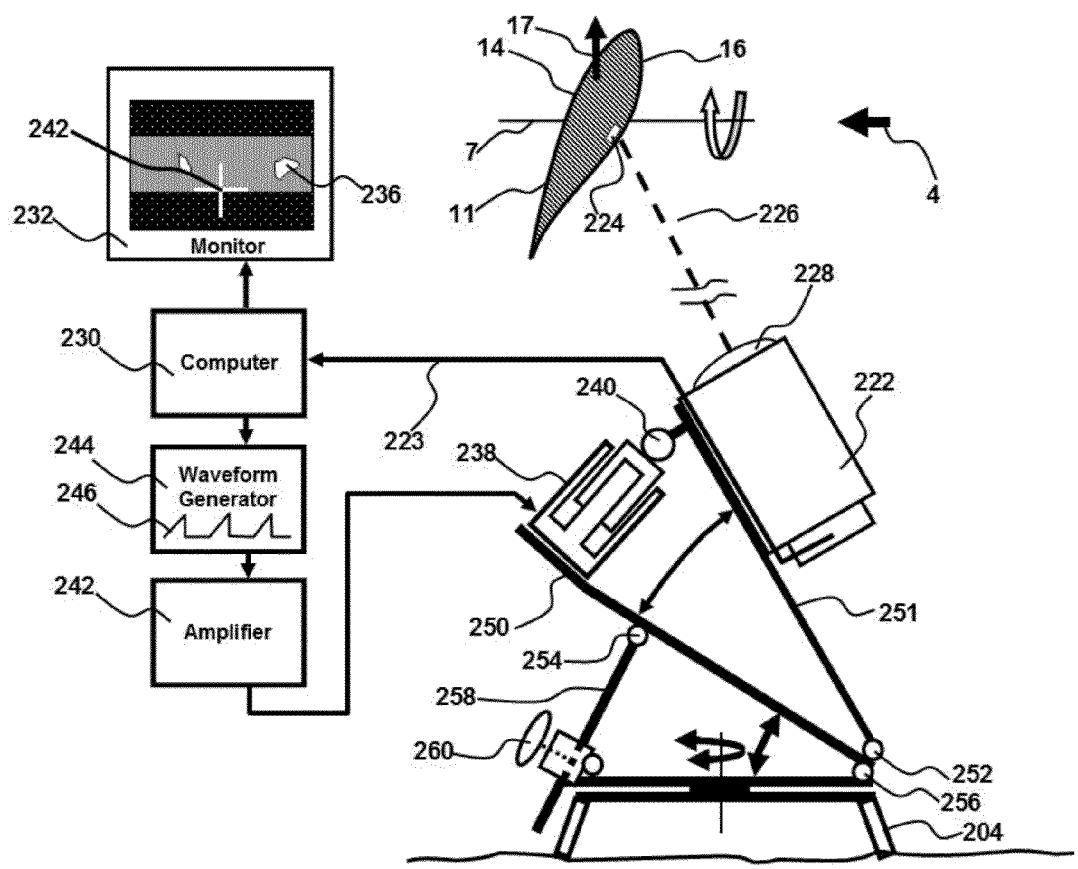
FIG. 9 is a schematic of computer controlled moving camera image stabilizer for derotating a sequence of thermal images of a rotating turbine blade using the presence of the blade in the video image to trigger the start of blade tracking.

FIG. 9 shows a second embodiment where the thermal camera 222 is moved in rotation to follow the blade 11 motion around axis 7. The thermal camera 222 is mounted on a frame or plate 251 and connected to hinge 252 which is also attached to frame member 250 which supports actuator 238. The opposite end of plate 251 is connected to the electric actuator through a flexible joint, such as a hinge or universal joint. The movement of the actuator causes the thermal camera 222 to move up and down which when aligned with a portion of the blade here the motion is substantially the same, will tend to stabilize the blade in the field of view of the thermal camera 222. Additional actuators can operate simultaneously to move the thermal camera in multiple directions however with additional complexity. In practice, one actuator is sufficient if a clear view of the blade 11 when it reaches the horizontal position during rotation can be attained in the field. Another option is to rotate the entire actuator 238, support plates 250 and 251 as well as the thermal camera 222 to align the motion of the actuator with the motion of the blade during data acquisition. Reducing the driven mass reduced vibration and power requirements for the electronics and electric actuator, which may be battery operated or power from the vehicle used by the operator. The motion of the camera should be align approximately with the direction as the motion of the turbine blade 11 in the camera field of view during it's rotation on axis 7.

Figure 10:
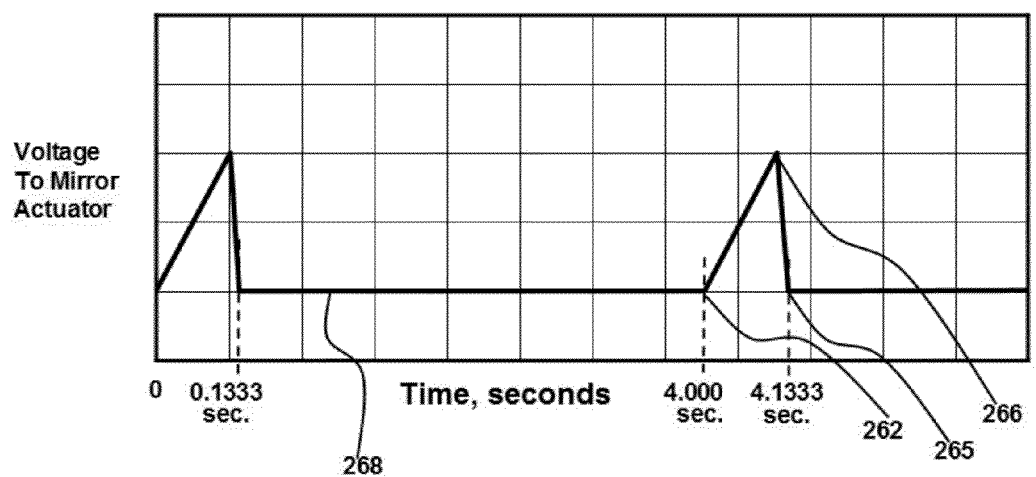
FIG. 10 shows the timing of the ramp voltage waveform used to drive the linear motor to drive the hinged plate supporting the thermal camera to track one blade only turing with a period of four seconds.

As the high pressure side of the blade, which viewed from the up wind side of the tower 6 at position 220 is turning clockwise, rises into the field of view of camera 222, the leading edge of the blade eventually crosses threshold marker 242. This motion can be identified as a change in the pixel intensity value from that of the open sky as seen by thermal camera 222, and the software electronically triggers the start of the motion of linear actuator 238 by computer 230 the waveform generator 244 and amplifier 242. Again, an optimal waveform is a ramp function which will move the camera 222 at a constant angular velocity to receive in lens 228 the thermal emissions 226 from the defect in the blade 224 as it moves vertically across the field of view at a constant velocity. This embodiment can also use a moving move a mirror. The tripod mount can also be fitted with a mechanical azimuth and elevation for example using rod 258 connected with a flexible joint 254 to the base frame for the camera 250 and locked with clamp 260 with the linear motor providing fine movement of the thermal camera or a mirror. Although the embodiment shown uses a tripod 204 to support the thermal camera and image de-rotation mechanism, any sturdy support can be used including a truck, van, car or a wheeled cart to easily move the equipment around the site of the wind turbine. FIG. 10 shows a graph of voltage vs time for the signal used to drive the image de-rotation actuator. For the manually operated de-rotation embodiment, the function generator operates continuously. The operator adjusts the repetition rate to match the turbine rotation period τ, 268. The ramp function shown in FIG. 10 has a 0.133 second duration to match the time for four video frames to be displayed. The electronic or software system can be designed to allow the operator to input these values directly and have the de-rotation device, using either the moving mirror 241 or the moving thermal camera configurations.

Figure 11:
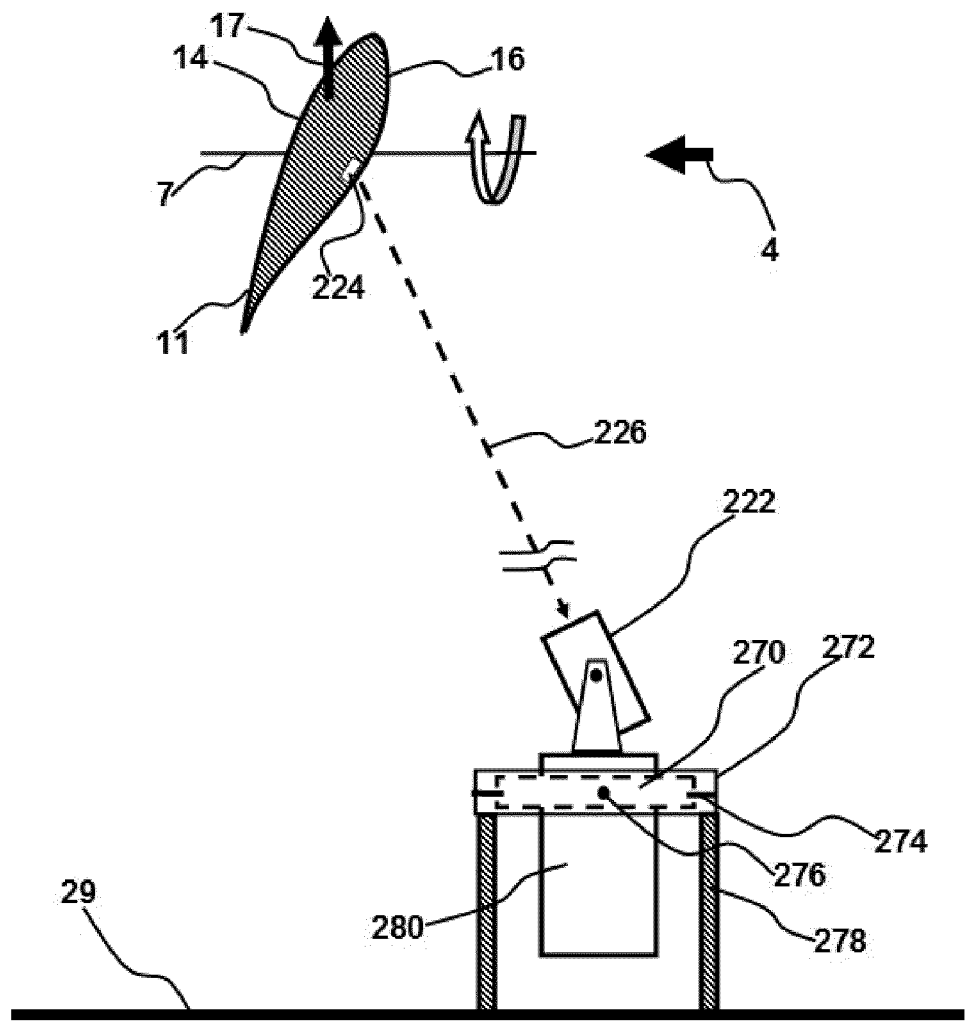
FIG. 11 is a schematic diagram of a gimbal mounted thermal camera for testing off shore wind turbine blades from a boat or ship.
Figure 12:
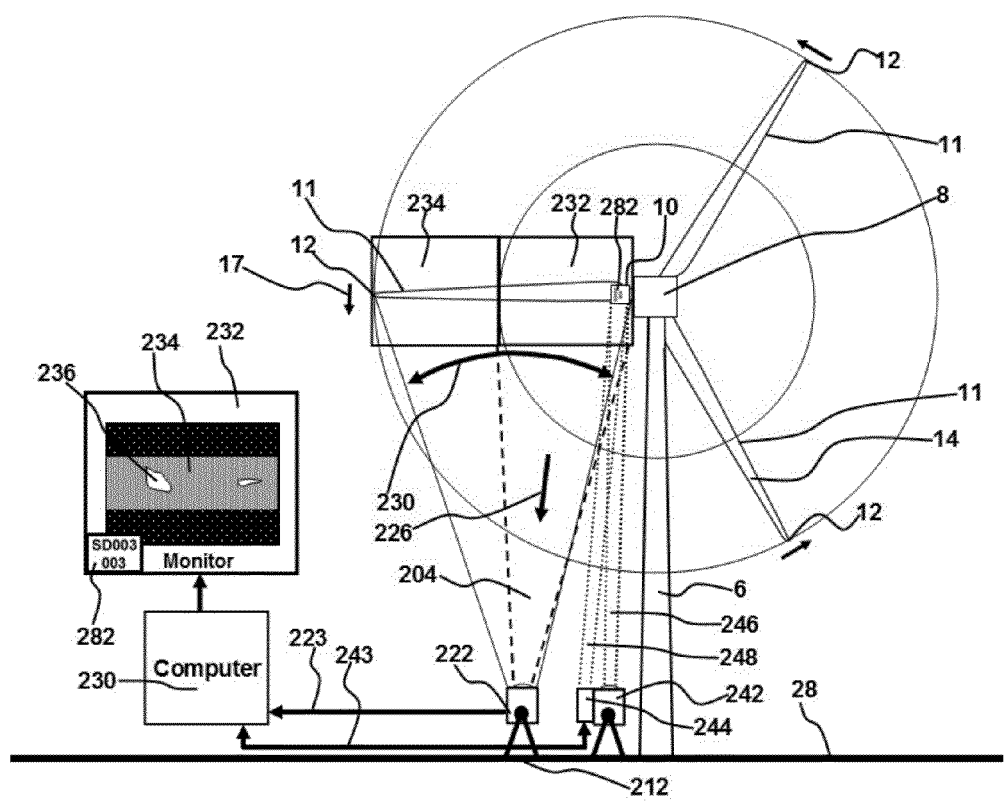
FIG. 12 is a schematic diagram of a thermal camera testing a blade with a visible light camera and light source to image the serial number of the blade and showing the image of the serial number presented with the test images of the blade.

FIG. 11 is a schematic drawing showing the addition of a gimbal mount to stabilize the thermal camera 222, and it's various motion mechanisms and embodiments described here in, during use on water aboard a ship or vessel to inspect blades 11 mounted on off shore wind power generators. In one embodiment, counter weight 280 is supported by gimbal mount comprised of inner frame 270 and outer frame 272 connected by bearing pins 274 and 276, as well as support housing or frame members 278 which is supported on the deck 29 of the ship or vessel. This allows camera 222 to remain aligned with blade 11 during inspections. This gimbal assembly may also be actively powered and use servo actuators and accelerometers, well know in the art, to provide a stabile platform with respect to the vessel rolling and pitching movement for successful operation of the blade inspection system described herein. In addition, the shipboard blade test system may use an inertia platform to keep the camera aimed at the target blade during tests to compensate for ship motion. FIG. 12 is a schematic diagram of the wind turbine blade inspection system described herein with the addition of a video recorder, camcorder, photographic camera or video camera 242 and a light source 244, configured to record the serial numbers 282 written on the root end 10 of each blade as it is tested. Frequently the optimal position for the thermal camera during the test is not the same position need to place the serial number camera to image the serial numbers. Any one of a number techniques may be used to synchronize the thermal images with the serial number images. First, a GPS clock and provide timing signals on the sound track of a video camcorder as well as timing signals to the thermal camera 222 or the computer 230, if connected at the time of data acquisition. Second, if the image de-rotator is being used an audible or electrical or visual signal can be sent by electrical line 243 to the serial number camera when the actuator begins to track the blade 11. A delay may be needed to time the serial number capture with the position of the blade to allow the blade to move from the test angle to the best angle to capture the correct serial number.

FIG. 13 shows two test results on operating 1.5 MW utility scale wind power generators made with embodiments of this invention. The top image shows seven video frames of one blade from the high pressure side as it rotates through the thermal camera field of view. The images were recorded as an .MOV file and played back through software that generates a peak store image. The trajectory 246 of the thermal emissions from an active propagating defect is seen as the blade rotates from top to bottom clockwise. The dark lines in the image of the high pressure side 14 of this blade are thermal camera 222 artifacts due to the fast blade 11 motion. The bottom image shows a test image of a leading edge of blade 11 that includes thermal response from hub 18 nacelle 8 and tower 6. The test was made from position 214 in FIG. 4. Two indications of defects 236 are seen. Scaling from known features in the image, the defects are located at 7.2 and 9 meters from the root end 10.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of remotely inspecting a wind turbine blade in situ, comprising:
   acquiring a continuous sequence of images of more than one wind turbine blade with a thermal imaging camera as each blade passes through a field of view of the thermal imaging camera while the turbine is rotating and undergoing cyclic load due to gravity and variations in wind loads and when the blades have substantially reached thermal equilibrium with ambient air after sunset in order to produce thermal imaging data;
   analyzing the thermal imaging data to identify atypical thermal patterns that could be indicative of frictional heating within or around defects within the wind turbine blades; and
   recording the images and creating a composite image of a selection of sequential blade images with a video peak-store program to track motion of a source of thermal emissions to distinguish between an actual thermal emitting area on the blade from unrelated thermal effects.

2. The method of remotely inspecting a wind turbine blade or blades according to claim 1, the thermal radiation being directed to the camera aperture by an image derotation device consisting of a moving mirror driven in multiple axes and multiple actuators using a microprocessor or computer generated waveform.

3. The method of remotely inspecting a wind turbine blade or blades according to claim 1, the thermal radiation being directed to the camera aperture by an image derotation device consisting of a moving mirror driven by multi-axis actuator to move a mirror to compensate for blade motion wherein the mirror is moved by an electric actuator using a microprocessor or computer generated waveform with an external trigger device to detect the blade position and initiate blade tracking thereby reducing degradation of the thermal image of the blade due to rotation.

4. The method of remotely inspecting a wind turbine blade or blades according to claim 1, the thermal radiation being directed to the camera aperture by an image derotation device consisting of a moving mirror driven by single actuator or multi-axis actuators to compensate for blade motion wherein the actuator(s) is(are) driven with electronically generated waveform with an electronic trigger signal from the thermal camera indicating the image of the rotating blade is entering the field of view of the thermal camera and initiate mirror actuation and blade tracking thereby reducing degradation of the thermal image of the blade due to said rotation.

5. The method of remotely inspecting a wind turbine blade or blades according to claim 1, whereby the thermal camera is mounted on a hinged supporting member with a vertical tilt actuator and drive electronics consisting of a waveform generator and amplifier to approximately track the blade image during a portion of the rotation thereby reducing the degrading effects of blade motion on the thermal camera image.

6. The method of remotely inspecting a wind turbine blade or blades according to claim 1, whereby the thermal camera is mounted on a hinged supporting member with a vertical tilt actuator with drive electronics consisting of a waveform generators and amplifier to track the blade image during a portion of an angular rotation with an electronic trigger signal from the thermal camera indicating the image of the rotating blade is entering the field of view of the thermal camera and to initiate a vertical camera actuation and to approximately track the blade thereby reducing degradation of the thermal image of the blade due to said rotation.

7. The method of remotely inspecting a wind turbine blade or blades according to claim 1, whereby the thermal camera is mounted on a hinged supporting member with a vertical tilt actuator and a horizontal pan actuator with drive electronics consisting of two waveform generators and amplifiers to track a portion of the blade image during rotation thereby reducing the thermal image degrading effects of blade motion.

8. The method of remotely inspecting a wind turbine blade or blades according to claim 1, whereby the thermal camera is mounted on a hinged supporting member with a vertical tilt actuator and a horizontal pan actuator with drive electronics consisting of two waveform generators and amplifiers with an electronic trigger signal from the thermal camera indicating the image of the rotating blade is entering the field of view of the thermal camera and initiate camera motion actuation and approximate blade tracking thereby reducing degradation of the thermal image of the blade due to said rotation.

9. The method of remotely inspecting a wind turbine blade according to claim 1, wherein a video image of blade serial numbers on the root end of the blade is recorded continuously with a video camera and an appropriate light illumination source and synchronized with video frames from a thermal camera imaging the blade for anomalies by using a sound signal that is recorded by the video camera and triggered manually by an operator when the defect appears on a video screen of the IR camera or computer thereby identifying the serial number of the blade with detected defects.

10. The method of remotely inspecting a wind turbine blade according to claim 1 wherein a video image of an illuminated view of blade serial numbers on the root end of the blade are recorded and synchronized with video frames from a thermal camera imaging the blade for anomalies, using GPS timing signals.

11. The method of remotely inspecting a wind turbine blade or blades according to claim 1, the thermal radiation being directed to the camera aperture by an image derotation device consisting of a moving mirror driven by an actuator to compensate for blade motion and resulting image degrading effects.

12. The method of remotely inspecting a wind turbine blade or blades according to claim 11, wherein the mirror is driven by an electric actuator using a function generator with manual controls for frequency, wave form and amplitude.

13. The method of remotely inspecting a wind turbine blade or blades according to claim 1, the thermal radiation being directed to the camera aperture by an image derotation device consisting of a moving mirror driven in multiple axes by multiple actuators to move a mirror to compensate for blade motion wherein the electric actuator is driven with two separate waveforms from two function generators with manual controls for frequency, wave form and amplitude.

14. The method of remotely inspecting a wind turbine blade or blades according to claim 13, wherein the waveform is a ramp or saw-tooth function.

15. A method of remotely inspecting a wind turbine blade in situ, the method comprising:
  imaging a portion of a wind turbine blade with a thermal imaging camera as the blade passes through a field of view of the thermal imaging camera while the turbine is rotating and undergoing cyclic load due to gravity and variations in wind loads and when the blade has substantially reached thermal equilibrium with ambient air after sunset in order to produce thermal imaging data; and
  analyzing the thermal imaging data to identify atypical thermal patterns that could be indicative of frictional heating within or around defects within the blade.

\* \* \* \* \*